United States Patent
Gupta et al.

(10) Patent No.: US 8,999,713 B2
(45) Date of Patent: Apr. 7, 2015

(54) METHODS OF MULTIPLYING CONIFER EMBRYOGENIC TISSUE

(75) Inventors: Pramod K. Gupta, Federal Way, WA (US); Diane G. Holmstrom, Bonney Lake, WA (US); Pamela L. Carlson, Federal Way, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 318 days.

(21) Appl. No.: 13/602,983

(22) Filed: Sep. 4, 2012

(65) Prior Publication Data

US 2013/0078722 A1 Mar. 28, 2013

Related U.S. Application Data

(60) Provisional application No. 61/540,429, filed on Sep. 28, 2011.

(51) Int. Cl.
*A01H 4/00* (2006.01)
*C12N 5/04* (2006.01)

(52) U.S. Cl.
CPC . *A01H 4/005* (2013.01); *C12N 5/04* (2013.01)

(58) Field of Classification Search
CPC ......... A01H 4/005; A01H 4/008; A01H 4/00; A01H 4/001; A01H 7/00; C12N 5/04; C12N 5/0025; C12N 5/00
USPC .................. 435/430.1, 422; 800/319, 294
See application file for complete search history.

(56) References Cited

U.S. PATENT DOCUMENTS

| | | | |
|---|---|---|---|
| 4,957,866 A | 9/1990 | Gupta et al. | |
| 5,034,326 A | 7/1991 | Pullman et al. | |
| 5,036,007 A | 7/1991 | Gupta et al. | |
| 5,041,382 A | 8/1991 | Gupta et al. | |
| 5,236,841 A | 8/1993 | Gupta et al. | |
| 5,294,549 A | 3/1994 | Pullman et al. | |
| 5,482,857 A | 1/1996 | Gupta et al. | |
| 5,491,090 A | 2/1996 | Handley, III et al. | |
| 5,563,061 A * | 10/1996 | Gupta | 435/422 |
| 5,564,224 A | 10/1996 | Carlson et al. | |
| 5,677,185 A | 10/1997 | Handley, III | |
| 5,687,504 A | 11/1997 | Carlson et al. | |
| 5,701,699 A | 12/1997 | Carlson et al. | |
| 5,821,126 A | 10/1998 | Durzan et al. | |
| 6,119,395 A | 9/2000 | Hartle et al. | |
| 7,906,334 B2 | 3/2011 | Denchev et al. | |

OTHER PUBLICATIONS

Bercetche et al. 14. Somatic embryogenesis in maritime pine. Somatic Embryogenesis in Woody Plants, vol. 3, 221-242, 1995.*
Filonova et al. Two waves of programmed cell death occur during formation and development of somatic embryos in the gymnosperm, Norway spruce. Journal of Cell Science 113, 4399-4411 (2000).*

\* cited by examiner

*Primary Examiner* — June Hwu

(74) *Attorney, Agent, or Firm* — Christensen O'Connor Johnson Kindness PLLC

(57) ABSTRACT

The invention provides methods for multiplying conifer embryogenic tissue. The methods of the invention comprise the steps of: (a) culturing conifer embryogenic tissue in or on a solid multiplication medium comprising one or more growth hormones; and (b) culturing the conifer embryogenic tissue multiplied in step (a) in or on a liquid multiplication medium comprising one or more growth hormones, wherein the initial concentration of growth hormones in the solid multiplication medium of step (a) is greater than the initial concentration of growth hormones in the liquid multiplication medium of step (b).

19 Claims, No Drawings

METHODS OF MULTIPLYING CONIFER EMBRYOGENIC TISSUE

CROSS-REFERENCE TO RELATED APPLICATION

This application is entitled to and claims the benefit of priority under 35 U.S.C. §119 from U.S. Provisional Patent Application Ser. No. 61/540,429 filed Sep. 28, 2011, and titled "Methods of Multiplying Conifer Embryogenic Tissue," the contents of which are incorporated herein by reference.

BACKGROUND

Modern silviculture often requires the planting of large numbers of genetically identical plants that have been selected to have advantageous properties. Production of new plants by sexual reproduction, which yields botanic seeds, is usually not feasible. Asexual propagation, via the culturing of somatic or zygotic embryos, has been shown for some species to yield large numbers of genetically identical embryos, each having the capacity to develop into a normal plant.

Somatic cloning is the process of creating genetically identical plants from plant tissue other than male and female gametes. In one approach to somatic cloning, plant tissue is cultured in an initiation medium that includes hormones, such as auxins and/or cytokinins, to initiate formation of embryogenic tissue, such as embryogenic suspensor masses, that are capable of developing into somatic embryos. Embryogenic suspensor mass, or ESM, has the appearance of a whitish translucent mucilaginous mass and contains early stage embryos. The embryogenic tissue is further cultured in a multiplication medium that promotes multiplication and mass production of the embryogenic tissue. The embryogenic tissue is then cultured in a development medium that promotes development and maturation of cotyledonary somatic embryos that can, for example, be placed on germination medium to produce germinants, and subsequently transferred to soil for further growth, or alternatively, placed within manufactured seeds and sown in soil where they germinate to yield seedlings. Manufactured seeds are described, for example, in U.S. Pat. Nos. 5,564,224; 5,687,504; 5,701,699; and 6,119,395.

The quality and growth rate of early stage embryos formed during the multiplication stage is directly related to the quality and quantity of cotyledonary embryos produced during the development period, and ultimately the quality and quantity of germinants and seedlings. The formation of early stage embryos of good quality during the multiplication stage increases the likelihood of formation of good quality cotyledonary embryos. Furthermore, good multiplication and growth rates are essential for the production of large numbers of cotyledonary embryos.

Therefore methods are needed to produce early stage embryos during the multiplication stage having good form and structure and good growth rate. The present invention addresses these and other needs.

SUMMARY

In one aspect the present invention provides methods of multiplying conifer embryogenic tissue comprising the steps of (a) culturing conifer embryogenic tissue in or on a first multiplication medium, wherein the first multiplication medium is a solid multiplication medium comprising one or more growth hormones, to multiply the conifer embryogenic tissue; and (b) culturing the conifer embryogenic tissue multiplied in step (a) in or on a second multiplication medium, wherein the second multiplication medium is a liquid multiplication medium comprising one or more growth hormones, to further multiply the conifer embryogenic tissue, wherein the initial concentration of growth hormones in the solid multiplication medium of step (a) is greater than the initial concentration of growth hormones in the liquid multiplication medium of step (b).

In one embodiment, the initial concentration of growth hormones in the solid multiplication medium of step (a) is about two to twelve times the initial concentration of growth hormones in the liquid multiplication medium of step (b). In one embodiment, the initial concentration of growth hormones in the solid multiplication medium of step (a) is about two to three times the initial concentration of growth hormones in the liquid multiplication medium of step (b). In one embodiment, the initial concentration of growth hormones in the solid multiplication medium of step (a) is about two to two and one half times the initial concentration of growth hormones in the liquid multiplication medium of step (b).

In one aspect, the methods of the invention further comprise culturing the conifer embryogenic tissue multiplied in step (b) in or on development medium to form conifer cotyledonary embryos.

DETAILED DESCRIPTION

Unless specifically defined herein, all terms used herein have the same meaning as they would to one skilled in the art of the present invention.

As used herein, the term "embryogenic suspensor mass" (ESM) refers to early stage embryos in the process of multiplication by budding and cleavage.

As used herein, the term "embryogenic tissue" refers to an aggregate of tens to hundreds of embryogenic cells that form an embryogenic suspensor mass.

As used herein, the term "explant" is a piece of tissue taken from a donor plant for culturing. Suitable sources of explants include, but are not limited to, tissue from cotyledons, hypocotyls, epicotyls, buds, meristematic centers for buds or roots, and seed embryos.

As used herein, the term "somatic embryo" refers to an embryo produced by culturing embryogenic tissue by standard methods under laboratory conditions in which the cells comprising the tissue are separated from one another and urged to develop into minute complete embryos.

As used herein, the term "cotyledonary embryo" refers to an embryo that possesses one or more cotyledons. Cotyledonary embryos have a well defined elongated bipolar structure with latent meristem with cotyledonary primordia at one end and a potential radicle at the opposite end. The cotyledonary structure frequently appears as a small "crown" at one end of the embryo.

The somatic embryogenesis process is a process to develop plant embryos in vitro. Methods for producing plant somatic embryos are known in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). Generally, the somatic embryogenesis process includes the steps of (1) initiation, sometimes referred to as induction, to initiate formation of embryogenic tissue, such as embryogenic suspensor mass (ESM), which is a white mucilaginous mass that includes early stage embryos having a long, thin-walled suspensor associated with a small head with dense cytoplasm and large nuclei; (2) multiplication, sometimes referred to as maintenance, to multiply and mass produce the embryogenic tissue; (3) development, to develop and form mature cotyledonary somatic embryos; and (4) post development steps such as singulation, stratification, germination, placement into manufactured seeds, and transferring to soil for further growth and development.

In the first step of the somatic embryogenesis process, a suitable conifer explant is first cultured in, or on, an induction medium. The induction medium generally includes inorganic salts and organic nutrient materials. For example, the induction medium may include maltose as a carbohydrate source. Examples of useful maltose concentrations are within the range from about 1% to about 5%, such as about 3%. The osmolality of the induction medium is typically about 160 mM/kg or even lower, but it may be as high as 170 mM/kg. The induction medium typically includes growth hormones. Examples of hormones that can be included in the induction medium are auxins (e.g., 2,4-dichlorophenoxyacetic acid (2,4-D), and naphthalene acetic acid) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 10 mg/L.

The induction medium may contain an adsorbent composition, especially when very high levels of growth hormones are used. The adsorbent composition can be any composition that is not toxic to the embryogenic cells at the concentrations utilized in the practice of the present methods, and that is capable of absorbing growth-promoting hormones, and toxic compounds produced by the plant cells, that are present in the medium. Non-limiting examples of useful adsorbent compositions include activated charcoal, soluble poly(vinyl pyrrolidone), insoluble poly(vinyl pyrrolidone), activated alumina, and silica gel. The adsorbent composition may be present in an amount, for example, from about 0.1 g/L to about 5 g/L.

The conifer explant tissue is typically cultured in, or on, an induction medium for a period of from 6 weeks to 12 weeks, to form conifer embryogenic tissue, sometimes referred to as embryogenic suspensor mass.

The embryogenic tissue is then transferred from the induction medium to multiplication medium to multiply and mass produce the embryogenic tissue.

The present invention provides methods of multiplying conifer embryogenic tissue. The methods of the present invention each includes the steps of (a) culturing conifer embryogenic tissue in or on a first multiplication medium, wherein the first multiplication medium is a solid multiplication medium comprising one or more growth hormones, to multiply the conifer embryogenic tissue; and (b) culturing the conifer embryogenic tissue multiplied in step (a) in or on a second multiplication medium, wherein the second multiplication medium is a liquid multiplication medium comprising one or more growth hormones, to further multiply the conifer embryogenic tissue, wherein the initial concentration of growth hormones in the solid multiplication medium of step (a) is greater than the initial concentration of growth hormones in the liquid multiplication medium of step (b).

In one embodiment, the initial concentration of growth hormones in the solid multiplication medium of step (a) is about two to twelve times the initial concentration of growth hormones in the liquid multiplication medium of step (b). In one embodiment, the initial concentration of growth hormones in the solid multiplication medium of step (a) is about two to three times the initial concentration of growth hormones in the liquid multiplication medium of step (b). In one embodiment, the initial concentration of growth hormones in the solid multiplication medium of step (a) is about two to two and one half times the initial concentration of growth hormones in the liquid multiplication medium of step (b).

Growth hormones suitable for use in the present invention include, but are not limited to, auxins and cytokinins. Auxins are plant growth hormones that promote cell division and growth. Exemplary auxins for use in the multiplication medium of the present invention include, but are not limited to, 2,4-dichlorophenoxyacetic acid (2,4-D), indole-3-acetic acid (IAA), indole-3-butyric acid (IBA), naphthalene acetic acid (NAA), and chlorogenic acid. Cytokinins are plant growth hormones that affect the organization of dividing cells. Exemplary cytokinins for use in the multiplication medium of the present invention include, but are not limited to, e.g., 6-benzylaminopurine (BAP), 6-furfurylaminopurine (kinetin), dihydrozeatin, zeatin, and zeatin riboside.

In one embodiment, the growth hormones in the multiplication medium of steps (a) and (b) are at least one of an auxin and a cytokinin. In one embodiment, the auxin is 2,4-dichlorophenoxyacetic acid. In one embodiment, the cytokinin is at least one of 6-benzylaminopurine and 6-furfurylaminopurine. In one embodiment, the multiplication medium of step (a) comprises two cytokinins. In one embodiment, the multiplication medium of step (b) comprises two cytokinins. In one embodiment, the two cytokinins are 6-benzylaminopurine and 6-furfurylaminopurine. In one embodiment, the auxin is 2,4-dichlorophenoxyacetic acid and the cytokinins are 6-benzylaminopurine and 6-furfurylaminopurine.

In one embodiment, the multiplication medium of steps (a) and (b) each comprises auxins and cytokinins. In one embodiment, the multiplication medium of steps (a) and (b) each comprises the growth hormones of 2,4-dichlorophenoxyacetic acid, 6-benzylaminopurine, and 6-furfurylaminopurine.

In one embodiment, the initial concentration of auxin in the solid multiplication medium of step (a) is from about 2.0 mg/L to about 5.0 mg/L. In one embodiment, the initial concentration of auxin in the solid multiplication medium of step (a) is from about 2.0 mg/L to about 3.0 mg/L.

In one embodiment, the total initial concentration of cytokinin in the solid multiplication medium of step (a) is from about 0.4 mg/L to about 0.5 mg/L. If more than one cytokinin is included in the solid multiplication medium of step (a), then the concentration of each cytokinin is such that the total initial concentration of cytokinin in the solid multiplication medium of step (a) is from about 0.4 mg/L to about 0.5 mg/L. For example, if two cytokinins are included in the solid multiplication medium of step (a), then the initial concentration of each cytokinin could be, for example, from about 0.2 mg/L to about 0.25 mg/L. Other combinations are also possible, for example, if the initial concentration of one cytokinin is about 0.1 mg/L, then the initial concentration of a second cytokinin could be from about 0.3 mg/L to about 0.4 mg/L.

In one embodiment, the initial concentration of auxin in the liquid multiplication medium of step (b) is from about 0.25 mg/L to about 1.1 mg/L. In one embodiment, the initial concentration of auxin in the liquid multiplication medium of step (b) is from about 0.5 mg/L to about 1.1 mg/L.

In one embodiment, the total initial concentration of cytokinin in the liquid multiplication medium of step (b) is from about 0.05 mg/L to about 0.2 mg/L. If more than one cytokinin is included in the liquid multiplication medium of step (b), then the concentration of each cytokinin is such that the total initial concentration of cytokinin in the liquid multiplication medium of step (b) is from about 0.05 mg/L to about 0.2 mg/L. For example, if two cytokinins are included in the liquid multiplication medium of step (b), then the initial concentration of each cytokinin could be, for example, from about 0.025 mg/L to about 0.1 mg/L. Other combinations are also possible, for example, if the initial concentration of one cytokinin is about 0.025 mg/L, then the initial concentration of a second cytokinin could be from about 0.025 mg/L to about 0.175 mg/L. In one embodiment, the total initial concentration of cytokinin in the multiplication medium of step (b) is from about 0.05 mg/L to about 0.1 mg/L.

In one embodiment, the initial concentration of auxin in the solid multiplication medium of step (a) is about three times the initial concentration of auxin in the liquid multiplication medium of step (b).

In one embodiment, the initial concentration of auxin in the solid multiplication medium of step (a) is about two times the initial concentration of auxin in the liquid multiplication medium of step (b).

In one embodiment, in which the auxin is 2,4-dichlorophenoxyacetic acid, the initial concentration of 2,4-dichlorophenoxyacetic acid in the solid multiplication medium of step (a) is about three times the initial concentration of 2,4-dichlorophenoxyacetic acid in the liquid multiplication medium of step (b).

In one embodiment, the initial concentration of 2,4-dichlorophenoxyacetic acid in the solid multiplication medium of step (a) is about two times the initial concentration of 2,4-dichlorophenoxyacetic acid in the liquid multiplication medium of step (b).

In one embodiment, the initial concentration of cytokinin in the solid multiplication medium of step (a) is about two and one-half times the initial concentration of cytokinin in the liquid multiplication medium of step (b).

In one embodiment, in which the cytokinin is 6-benzylaminopurine, the initial concentration of 6-benzylaminopurine in the solid multiplication medium of step (a) is about two and one-half times the initial concentration of 6-benzylaminopurine in the liquid multiplication medium of step (b).

In one embodiment, in which the cytokinin is 6-furfurylaminopurine, the initial concentration of 6-furfurylaminopurine in the solid multiplication medium of step (a) is about two and one-half times the initial concentration of 6-furfurylaminopurine in the liquid multiplication medium of step (b).

In one embodiment, the initial concentration of 2,4-dichlorophenoxyacetic acid in the solid multiplication medium of step (a) is about three times the initial concentration of 2,4-dichlorophenoxyacetic acid in the liquid multiplication medium of step (b); the initial concentration of 6-benzylaminopurine in the solid multiplication medium of step (a) is about two and one-half times the initial concentration of 6-benzylaminopurine in the liquid multiplication medium of step (b); and the initial concentration of 6-furfurylaminopurine in the solid multiplication medium of step (a) is about two and one-half times the initial concentration of 6-furfurylaminopurine in the liquid multiplication medium of step (b).

The multiplication medium is formulated to promote the growth and multiplication of conifer embryogenic tissue, such as embryonal suspensor mass. In addition to growth hormones, which promote cell division and growth of the embryogenic tissue, such as auxins and/or cytokinins, as described supra, the multiplication medium contains nutrients that sustain the embryogenic tissue. The osmolality of the multiplication medium is typically in the range of 120-250 mM/kg.

It is generally desirable, though not essential, to include maltose as the sole, or principal, metabolizable sugar source in the multiplication medium. Examples of useful maltose initial concentrations are within the range of from about 1% to about 2.5%. Examples of suitable multiplication media for use in the present invention are set forth in Example 1 herein.

In the methods of the present invention, conifer embryogenic tissue is cultured in, or on, solid multiplication medium and further cultured on liquid multiplication medium at a temperature of from 10° C. to 30° C., such as from 15° C. to 25° C., or such as from 20° C. to 23° C. Conifer embryogenic tissue is typically transferred to fresh multiplication medium once per week, bi-weekly, or as growth exhausts media components.

The embryogenic tissue is typically cultured on solid multiplication medium for a period of time sufficient to produce from about 50 mg to about 250 mg fresh weight biomass, before transferring the embryogenic tissue to liquid multiplication medium. Fresh weight can be determined by removing the embryogenic tissue or ESM from the underlying solid media and weighing the tissue, without first subjecting it to a drying process to remove moisture content. However, the embryogenic tissue can remain on solid multiplication medium, with subculturing to fresh solid medium, for longer periods of time to produce larger amounts of biomass, for example for use in a bioreactor.

The embryogenic tissue is subsequently transferred to liquid multiplication medium and can remain in liquid multiplication medium, with subculture to fresh medium, indefinitely, depending on production needs. The embryogenic tissue can remain in liquid multiplication medium for up to six months, up to one year, or longer.

In one aspect, the methods of the invention further comprise transferring the multiplied conifer embryogenic tissue to development medium and culturing the conifer embryogenic tissue on development medium to form conifer cotyledonary embryos. Suitable development medium contains nutrients that sustain the somatic embryos. Maltose and glucose may be included in the development medium as the principal sources of sugar for the somatic embryos. Useful maltose and glucose initial concentrations are within the range of from about 1% to about 2.5%. Suitable development media typically do not include growth-promoting hormones, such as auxins and cytokinins, but may include the hormone abscisic acid. When abscisic acid is utilized in the development medium, it is typically utilized at an initial concentration in the range of from about 1 mg/L to about 200 mg/L. The development medium may contain gellan gum, typically present at an initial concentration of up to about 0.40%. The osmolality of the development medium can be adjusted to a value that falls within a desired range, using osmoticants such as PEG 8000 molecular weight, such as from about 250 mM/Kg to about 450 mM/Kg. Typically, an osmolality of 300-350 mM or higher is advantageous.

After the development period, the cotyledonary somatic embryos can optionally be transferred to a maturation medium, and then subjected to post development steps such as singulation, stratification, germination, placement into manufactured seeds, and transferring to soil for further growth and development.

In one aspect, the methods of the invention comprise the steps of: (a) culturing conifer explants on induction medium to form conifer embryogenic tissue; (b) culturing the conifer embryogenic tissue formed in step (a) in or on a first multiplication medium, wherein the first multiplication medium is a solid multiplication medium comprising one or more growth hormones, to multiply the conifer embryogenic tissue; (c) culturing the conifer embryogenic tissue multiplied in step (b) in or on a second multiplication medium, wherein the second multiplication medium is a liquid multiplication medium comprising one or more growth hormones, to further multiply the conifer embryogenic tissue, wherein the initial concentration of growth hormones in the solid multiplication medium of step (b) is greater than the initial concentration of growth hormones in the liquid multiplication medium of step (c); and (d) culturing the embryogenic tissue multiplied in step (c) on development medium to form conifer cotyledonary embryos.

The methods of the invention improve the growth rate and quality of conifer embryogenic tissue at the multiplication stage, as shown in Examples 3-4.

The methods of the invention produce a higher yield of cotyledonary embryos of a more consistent quality compared to an otherwise identical method in which the initial concentration of growth hormones in the solid multiplication medium and the initial concentration of growth hormones in the liquid multiplication medium are the same.

For example, as shown in Example 3, a method of culturing embryogenic tissue on solid multiplication medium, followed by culturing in liquid multiplication medium, in which the initial concentration of growth hormones in the solid multiplication medium was about three times the initial concentration of growth hormones in the liquid multiplication medium, yielded about twice the number of embryos and germinants, compared to the control method, in which the initial concentration of growth hormones in the solid multiplication medium was the same as the initial concentration of growth hormones in the liquid multiplication medium.

Similarly, as shown in Example 4, a method of culturing embryogenic tissue on solid multiplication medium, followed by culturing in liquid multiplication medium, in which the initial concentration of growth hormones in the solid multiplication medium was about three times the initial concentration of growth hormones in the liquid multiplication medium, yielded increased fresh weight and settled cell volume, compared to the control method, in which the initial concentration of growth hormones in the solid multiplication medium was the same as the initial concentration of growth hormones in the liquid multiplication medium.

The methods of the invention are particularly suitable for multiplying embryogenic tissue of plants of the order Coniferales, including, species within the families Pinaceae, Cupressaceae, and Taxodiaceae. Most or all species within the genera *Pinus, Picea, Tsuga, Pseudotsuga, Thuja, Juniperis, Larix,* and *Sequoia* are believed to be well suited for multiplication by the present method.

The following examples are provided for the purpose of illustrating, not limiting, the invention.

EXAMPLES

Example 1

This example shows the compositions of multiplication media used in the examples that follow. Table 1 provides the components of basic multiplication medium. Table 2 provides the components of each multiplication medium that are in addition to the basic multiplication medium.

TABLE 1

Formulation of Basic Multiplication Media (BM)

| Media Component | Initial concentration (mg/L) |
| --- | --- |
| Salts | |
| $NH_4NO_3$ | 150 |
| $KNO_3$ | 909.9 |
| $Ca(NO_3)_2$—$4H_2O$ | 236.15 |
| $MgSO_4$—$7H_2O$ | 246.5 |

TABLE 1-continued

Formulation of Basic Multiplication Media (BM)

| Media Component | Initial concentration (mg/L) |
| --- | --- |
| $Mg(NO_3)_2$—$6H_2O$ | 256.5 |
| $MgCl_2$—$6H_2O$ | 50 |
| $KH_2PO_4$ | 136 |
| $CaCl_2$—$2H_2O$ | 50 |
| KI | 4.15 |
| $H_3BO_3$ | 15.5 |
| $MnSO_4$—$H_2O$ | 10.5 |
| $ZnSO_4$—$7H_2O$ | 14.4 |
| $Na_2MoO_4$—$2H_2O$ | 0.125 |
| $CuSO_4$—$5H_2O$ | 0.125 |
| $CoCl_2$—$6H_2O$ | 0.125 |
| $FeSO_4$—$7H_2O$ | 27.87 |
| $Na_2EDTA$ | 37.26 |
| Vitamins/Amino Acids | |
| Nicotinic acid | 0.5 |
| Pyridoxine HCl | 0.5 |
| Thymine HCl | 1 |
| Glycine | 2 |
| Solutes | |
| Myo-Inositol | 200 |
| Casein hydrolysate | 500 |
| L-glutamine | 1000 |
| Maltose | 30000 |

TABLE 2

Formulations of Multiplication Media used in the Examples

| | Component* (mg/L) | | | |
| --- | --- | --- | --- | --- |
| Media | 2,4-D | KINETIN | BAP | GELLAN GUM |
| BM1 | 1.1 | 0.1 | 0.1 | 1600 |
| BM2 | 3.0 | 0.25 | 0.25 | 1600 |
| BM3 | 2.0 | 0.2 | 0.2 | 1600 |
| BM4 | 1.1 | 0.1 | 0.1 | |
| BM5 | 0.25 | 0.025 | 0.025 | |
| BM6 | 0.5 | 0.05 | 0.05 | |
| BM7 | 2.0 | 0.2 | 0.2 | |

*2,4D (2,4-dichlorophenoxyacetic acid)
Kinetin (6-furfurylaminopurine)
BAP (6-benzylaminopurine)

Example 2

This example shows the effects of different initial concentrations of growth hormones in liquid multiplication medium on the growth and quality of Loblolly pine embryogenic tissue.

Two genotypes of Loblolly pine embryogenic suspensor mass (ESM) cultures were maintained in liquid multiplication media BM4, BM5, BM6, and BM7 (as described in Example 1), for seven weeks, and were subcultured every week. After the fourth subculture, and weekly through the seventh subculture, ESM growth was measured by settled cell volume (SCV), and embryo quality was assessed under microscope by noting the presence of organized smooth embryonal heads and suspensors, signs of stress (white heads versus translucent heads), and browning.

Results.

Higher initial concentrations of growth hormones in BM7 liquid multiplication medium was found to inhibit ESM growth and the embryos showed signs of stress as compared to the standard BM4 liquid multiplication medium.

Lower initial concentrations of growth hormones in BM5 and BM6 liquid multiplication media did not result in significant differences in ESM growth or quality as compared to the standard BM4 liquid multiplication medium.

Initial concentrations of 0.25 mg/L to 1.1 mg/L of 2,4-D; 0.025 mg/L to 0.1 mg/L Kinetin; and 0.025 mg/L to 0.1 mg/L of BAP in liquid multiplication media appeared to work equally well for maintaining and multiplying pine embryogenic tissue.

Example 3

This example shows the effects of different initial concentrations of growth hormones in solid multiplication medium on the growth and quality of Loblolly pine embryogenic tissue.

Loblolly pine embryogenic suspensor mass were multiplied on BM1 or BM2 solid multiplication medium (as described in Example 1). The initial concentration of auxin in BM2 was about three times the initial concentration of auxin in BM1, and initial concentration of each cytokinin in BM2 was about two and one-half times the initial concentration of cytokinin in BM1.

After a sufficient amount of growth had occurred, ESM was transferred to liquid multiplication medium BM4 (as described in Example 1) for three weeks. The initial concentration of auxins and cytokinins in liquid multiplication medium BM4 was the same as in solid multiplication medium BM1. ESM was then removed from the BM4 medium, rinsed, and plated onto solid development medium for 12 weeks. Following cold treatment and conditioning over water, the embryos were transferred to germination medium.

Results.

ESM cultured on solid multiplication medium BM2 were slightly more prolific and healthy than ESM cultured on solid multiplication medium BM1. As shown in Table 3 below, about twice the number of embryos resulted from ESM cultured on solid multiplication medium BM2 than from ESM cultured on solid multiplication medium BM1. Because the number of embryos resulting from ESM cultured on solid multiplication medium BM2 was higher than from ESM cultured on solid multiplication medium BM1, the number of germinants obtained from ESM cultured on solid multiplication medium BM2 was also higher than from ESM cultured on solid multiplication medium BM1.

TABLE 3

| Media | Average Embryo Yield | Number of Germinants |
|-------|---------------------|----------------------|
| BM1   | 40                  | 27                   |
| BM2   | 80                  | 46                   |

As the data in Table 3 shows, a method of culturing ESM on solid multiplication medium, followed by culturing in liquid multiplication medium, in which the initial concentration of growth hormones in the solid multiplication medium was about three times the initial concentration of growth hormones in the liquid multiplication medium, improved embryo yield, and the yield of germinants, compared to a control method of culturing ESM on solid multiplication medium, followed by culturing in liquid multiplication medium, in which the initial concentration of growth hormones in the solid multiplication medium was the same as the initial concentration of growth hormones in the liquid multiplication medium.

ESM appeared to benefit from a two-step multiplication method in which ESM are first cultured on solid multiplication medium, followed by culturing in liquid multiplication medium, in which the initial concentration of growth hormones in the solid multiplication medium is about three times the initial concentration of growth hormones in the liquid multiplication medium.

Example 4

This example shows the effects of different initial concentrations of growth hormones in solid multiplication medium on the growth and quality of Loblolly pine embryogenic tissue.

Step A.

Loblolly pine ESM from three different genotypes, Genotype A, Genotype B, and Genotype C were multiplied on BM1, BM2, or BM3 solid multiplication medium (as described in Example 1) for nine weeks. At the beginning of the experiment, each plate of solid medium contained four lentil-sized clumps of ESM of about 5 mm in diameter and weighing an estimated 100 mg each. Lentil-sized cultures of new growth were transferred to fresh solid medium every three weeks.

At the end of the nine-week period, the growth and quality of the ESM was assessed. A visual assessment determined that ESM multiplied on BM2 solid medium had the most growth and browned the least.

Photographs of each plate were taken and the fresh weight of each clump of ESM was estimated by the following method. The mean diameter of each clump was determined by averaging the measurement of two axes, which yielded an estimated area in mm$^2$. The fresh weight was estimated by multiplying the estimated area by a conversion factor of 3.2 mg/mm$^2$. The data is summarized in Table 4.

TABLE 4

| Genotype | Medium | Clump Diameter (mm) | Mean clump diameter (mm) | Standard deviation | Estimated mean fresh weight per clump (mg) |
|----------|--------|---------------------|--------------------------|--------------------|---------------------------------------------|
| A | BM1 | 12.0 | 12.0 | 1.19 | 364 |
|   | BM1 | 13.2 |      |      |     |
|   | BM1 | 10.8 |      |      |     |
|   | BM3 | 12.0 | 11.7 | 0.42 | 342 |
|   | BM3 | 11.4 |      |      |     |
|   | BM3 |      | Not measured |  |     |
|   | BM2 | 12.6 | 13.6 | 0.91 | 463 |
|   | BM2 | 14.4 |      |      |     |
|   | BM2 | 13.8 |      |      |     |
| B | BM1 | 7.4  | 8.3  | 1.65 | 176 |
|   | BM1 | 10.2 |      |      |     |
|   | BM1 | 7.2  |      |      |     |
|   | BM3 | 10.2 | 8.0  | 1.92 | 166 |
|   | BM3 | 7.2  |      |      |     |
|   | BM3 | 6.6  |      |      |     |
|   | BM2 | 17.9 | 15.9 | 2.95 | 653 |
|   | BM2 | 17.3 |      |      |     |
|   | BM2 | 12.6 |      |      |     |
| C | BM1 | 10.2 | 11.4 | 0.99 | 327 |
|   | BM1 | 12.0 |      |      |     |
|   | BM1 | 12.0 |      |      |     |
|   | BM3 | 12.6 | 12.8 | 1.50 | 412 |
|   | BM3 | 14.3 |      |      |     |
|   | BM3 | 11.4 |      |      |     |
|   | BM2 | 14.3 | 14.9 | 0.60 | 562 |
|   | BM2 | 15.5 |      |      |     |
|   | BM2 | 14.9 |      |      |     |

Results.

For all three genotypes, the most growth, as measured in fresh weight biomass, at the end of the nine-week period, occurred in ESM that were cultured on solid multiplication medium BM2, which had the highest initial concentrations of growth hormones. For Genotypes A and B, the amount of growth observed in ESM cultured on solid multiplication media BM1 and BM3 was about the same, even though the initial concentration of growth hormones in medium BM3 is about twice the initial concentration of growth hormones in medium BM1. However, Genotype C ESM cultured on medium BM3 showed higher growth than ESM cultured on medium BM1.

Step B.

After nine weeks growth on solid multiplication medium, as described in Step A, samples of ESM of each genotype that had been cultured on solid multiplication media BM1 and BM2 were transferred to liquid multiplication medium BM4 (as described in Example 1). The ESM were cultured in liquid multiplication medium for four weeks and were subcultured weekly. The amount of settled cell volume (SCV) was measured in milliliters at the end of each week. The data is summarized in Table 5 and shows the amount of settled cell volume gained for each culture at the end of the week.

TABLE 5

| Week in Culture | Solid Maintenance Medium | Genotype A | Genotype B | Genotype C |
|---|---|---|---|---|
| 1 | BM1 | 0 | 0 | 0 |
|   | BM2 | 8 | 10 | 8 |
| 2 | BM1 | 0 | 0 | 0 |
|   | BM2 | 8 | 27 | 12 |
| 3 | BM1 | 10 | 0 | 18 |
|   | BM2 | 19 | 22 | 17 |
| 4 | BM1 | 13 | 5 | 13 |
|   | BM2 | 17 | 19 | 21 |

Results.

In all three genotypes, ESM grown on solid multiplication medium BM1 required a week to start growing in liquid multiplication medium, while ESM grown on solid multiplication medium BM2 started growing the first week. BM2 cultures continued to grow faster, as measured in settled cell volume, than BM1 cultures, and showed less browning, and exhibited slightly better quality.

A method of culturing ESM on solid multiplication medium, followed by culturing in liquid multiplication medium, in which the initial concentration of growth hormones in the solid multiplication medium is about three times the initial concentration of growth hormones in the liquid multiplication medium increased the growth rate of ESM and resulted in less browning than a control method of culturing ESM on solid multiplication medium, followed by culturing in liquid multiplication medium, in which the initial concentration of growth hormones in the solid multiplication medium and liquid multiplication medium is the same.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of multiplying conifer embryogenic tissue comprising the steps of:
   (a) culturing conifer embryogenic tissue in or on a first multiplication medium, wherein the first multiplication medium is a solid multiplication medium comprising one or more growth hormones, to multiply the conifer embryogenic tissue; and
   (b) culturing the conifer embryogenic tissue multiplied in step (a) in or on a second multiplication medium, wherein the second multiplication medium is a liquid multiplication medium comprising one or more growth hormones, to further multiply the conifer embryogenic tissue,
   wherein the initial concentration of the growth hormones in the solid multiplication medium of step (a) is about two to about three times the initial concentration of the growth hormones in the liquid multiplication medium of step (b).

2. The method of claim 1, wherein the initial concentration of the growth hormones in the solid multiplication medium of step (a) is about two to about two and one-half times the initial concentration of the growth hormones in the liquid multiplication medium of step (b).

3. The method of claim 1, wherein the growth hormones in the multiplication medium of steps (a) and (b) are at least one of an auxin and a cytokinin.

4. The method of claim 3, wherein the initial concentration of auxin in the solid multiplication medium of step (a) is from about 2.0 mg/L to about 5.0 mg/L.

5. The method of claim 3, wherein the initial concentration of auxin in the solid multiplication medium of step (a) is from about 2.0 mg/L to about 3.0 mg/L.

6. The method of claim 3, wherein the initial concentration of cytokinin in the solid multiplication medium of step (a) is from about 0.2 mg/L to about 0.25 mg/L.

7. The method of claim 3, wherein the initial concentration of auxin in the liquid multiplication medium of step (b) is from about 0.25 mg/L to about 1.1 mg/L.

8. The method of claim 3, wherein the initial concentration of cytokinin in the liquid multiplication medium of step (b) is from about 0.025 mg/L to about 0.1 mg/L.

9. The method of claim 3, wherein the auxin is 2,4-dichlorophenoxyacetic acid.

10. The method of claim 3, wherein the cytokinin is at least one of 6-benzylaminopurine and 6-furfurylaminopurine.

11. The method of claim 3, wherein the multiplication medium of step (a) and step (b) each comprises the growth hormones of 2,4-dichlorophenoxyacetic acid, 6-benzylaminopurine, and 6-furfurylaminopurine.

12. The method of claim 9, wherein the initial concentration of 2,4-dichlorophenoxyacetic acid in the solid multiplication medium of step (a) is about three times the initial concentration of 2,4-dichlorophenoxyacetic acid in the liquid multiplication medium of step (b).

13. The method of claim 10, wherein the initial concentration of 6-benzylaminopurine in the solid multiplication medium of step (a) is about two and one-half times the initial concentration of 6-benzylaminopurine in the liquid multiplication medium of step (b).

14. The method of claim 10, wherein the initial concentration of 6-furfurylaminopurine in the solid multiplication medium of step (a) is about two and one-half times the initial concentration of 6-furfurylaminopurine in the liquid multiplication medium of step (b).

15. The method of claim 11, wherein the initial concentration of 2,4-dichlorophenoxyacetic acid in the solid multiplication medium of step (a) is about three times the initial concentration of 2,4-dichlorophenoxyacetic acid in the liquid multiplication medium of step (b); the initial concentration of 6-furfurylaminopurine in the solid multiplication medium of step (a) is about two and one-half times the initial concentration of 6-furfurylaminopurine in the liquid multiplication medium of step (b); and the initial concentration of 6-benzylaminopurine in the solid multiplication medium of step (a) is about two and one-half times the initial concentration of 6-benzylaminopurine in the liquid multiplication medium of step (b).

16. The method of claim 1, further comprising culturing the conifer embryogenic tissue in or on the solid multiplication medium of step (a) for a period of time to produce about 50 mg to about 250 mg fresh weight biomass.

17. The method of claim 1, further comprising culturing the conifer embryogenic tissue multiplied in step (b) in or on development medium to form conifer cotyledonary embryos.

18. The method of claim 1, wherein the conifer embryogenic tissue is pine embryogenic tissue.

19. The method of claim 18, wherein the pine embryogenic tissue is Loblolly pine embryogenic tissue.

* * * * *